United States Patent [19]
Krukenberg

[11] Patent Number: 5,755,813
[45] Date of Patent: May 26, 1998

[54] PROSTHETIC BRAKE JOINT

[75] Inventor: Manfred Krukenberg, Duderstadt, Germany

[73] Assignee: Otto Bock Orthopaedische Industrie Besitz-Und Verwaltungs-Kommanditgesellschaft, Duderstadt, Germany

[21] Appl. No.: 623,038

[22] Filed: Mar. 28, 1996

[30] Foreign Application Priority Data

Mar. 31, 1995 [DE] Germany ............... 195 11 890.1

[51] Int. Cl.⁶ ............................................ A61F 2/64
[52] U.S. Cl. ............................ 623/44; 623/43; 623/45
[58] Field of Search ............................. 623/39, 40, 43, 623/44, 45, 46

[56] References Cited

U.S. PATENT DOCUMENTS

| | | | |
|---|---|---|---|
| 2,519,226 | 8/1950 | Coe | 623/44 |
| 3,015,825 | 1/1962 | Blatchford | |
| 3,863,274 | 2/1975 | Glabiszewski | |
| 4,152,787 | 5/1979 | Megsyesy | 623/44 |
| 4,997,449 | 3/1991 | Prahl et al. | 623/46 |
| 5,545,233 | 8/1996 | Fitzlaff | 623/46 |

FOREIGN PATENT DOCUMENTS 1 766 309  7/1971  Germany.
2 228 391  12/1973  Germany.

*Primary Examiner*—John G. Weiss
*Assistant Examiner*—Bruce E. Snow
*Attorney, Agent, or Firm*—Foley & Lardner

[57] ABSTRACT

A prosthetic brake joint includes an upper joint portion, a lower joint portion, and a joint shaft which pivotably connects the two joint portions together. The joint shaft, designed as a brake shaft, is connected to the lower joint portion for fixed rotation with the lower joint portion. A brake bushing surrounds and rotates about the joint shaft and operates as a bearing. The brake bushing is connected to a clamping or support portion for fixed rotation with the clamping or support portion. The upper joint portion is mounted to the clamping or support portion in an articulated manner via a pivot axle. Under loading, the upper joint portion impacts the clamping or support portion and thus the brake bushing, and thereby exerts a braking force on the joint shaft. The brake bushing is surrounded by an annular brake chamber which is filled with an incompressible medium. The annular brake chamber communicates, for purposes of fluid exchange, with a closed hollow space integrated in the clamping or support portion. A pressure piston supports the upper joint portion and protrudes into the closed hollow space to impact the incompressible medium which compresses the brake bushing against the joint shaft to brake rotation of the prosthetic knee joint.

9 Claims, 5 Drawing Sheets

PROSTHETIC BRAKE JOINT

BACKGROUND OF THE INVENTION

This invention relates to a brake joint for prostheses. More specifically, this invention relates to a knee brake joint for leg prostheses.

Brake joints for prostheses generally include an upper joint portion, a lower joint portion, and a joint shaft which connects the two joint portions pivotably to one another. The lower joint portion is connected to the joint shaft for fixed rotation with the joint shaft. The joint shaft is designed as, and operates as, a brake shaft. The joint shaft is surrounded by a brake bushing which rotates upon the joint shaft and serves as a bearing. A clamping or support portion connects to the brake bushing for fixed rotation with the brake bushing. The upper joint portion is mounted to the clamping or support portion in an articulated manner via a pivot axle in such a way that the upper joint portion, under loading, impacts the clamping or support portion and thus the brake bushing, and thereby exerts a braking force on the joint shaft.

One type of prosthetic brake joint is disclosed in German Patent No. 22 28 391. In such a construction, the clamping or support portion of the knee brake joint is designed as, and operates as, a clamping lever. The clamping lever supports an upper joint portion, and, under loading, the clamping lever directly impacts the brake bushing. This increases the friction between the brake pushing and the joint shaft acting as brake shaft. Thus, braking occurs by actuation of the joint (brake) shaft by the clamping lever via the brake bushing. The subject invention improves upon the prosthetic brake joint of the type disclosed in German Patent No. 22 28 391.

Accordingly, it is therefore a general object of the invention to provide a prosthetic brake joint which transfers braking force from a brake bushing to a joint shaft by compression of the brake bushing, rather than actuation of the brake bushing.

It is a specific object of the invention to provide a prosthetic brake joint which applies force uniformly to the circumference of the brake bushing and thus applies force uniformly from the brake bushing onto the joint shaft.

It is another object of the invention to provide a prosthetic brake joint which achieves high braking performance, even at low braking pressure.

It is still another object of the invention to provide a prosthetic brake joint which reduces wear and tear on the prosthetic brake joint components.

It is a further object of the invention to provide a prosthetic brake joint which enables pretensioning and resetting of the prosthetic brake joint.

It is yet a further object of the invention to provide a prosthetic brake joint which is stable and has a high rigidity of connection.

SUMMARY OF THE INVENTION

A preferred embodiment of the invention which is intended to accomplish at least some of the foregoing objects includes a prosthetic brake joint with an upper joint portion, a lower joint portion, and a joint shaft pivotably connecting the upper and lower joint portions to one another. The lower joint portion connects to the joint shaft for fixed rotation with the joint shaft. A brake bushing surrounds the joint shaft. The brake bushing runs upon the joint shaft and operates as a bearing. A clamping or support portion connects to the brake bushing for fixed rotation with the brake bushing. A pivot axle mounts the upper joint portion on the clamping or support portion in an articulated manner in such a way that the upper joint portion, under loading, impacts on the clamping or support portion and thus the brake bushing, thereby exerting a braking force on the joint shaft. An annular brake chamber surrounds the brake bushing. The annular brake chamber is filled with an incompressible medium and communicates, for purposes of fluid exchange, with a closed hollow space. The closed hollow space is integrated in the clamping or support portion. A pressure piston protrudes into the closed hollow space. The pressure piston impacts the incompressible medium and supports the upper joint portion.

In the subject invention, the brake bushing is surrounded by an annular brake chamber which is filled with an incompressible medium. The annular brake chamber communicates, for purposes of fluid exchange, with a closed hollow space in a clamping or support portion of the knee joint brake. A pressure piston, which supports the upper joint portion, protrudes into the closed hollow space and impacts, or contacts, the incompressible medium.

As seen in conventional prosthetic brake joints, the brake joint is activated by pressing on a brake mechanism. Like conventional prosthetic brake joints, friction is transmitted from a brake bushing onto a brake shaft. Unlike conventional prosthetic brake joints, however, the subject invention transfers braking force to the brake shaft by compression of the brake bushing, rather than actuation of the brake bushing. Compression of the brake bushing is effected, according to the invention, by use of an incompressible medium, for example, oil.

Additional objects and advantages of the invention will be set forth in the description which follows, and in portion will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a portion of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
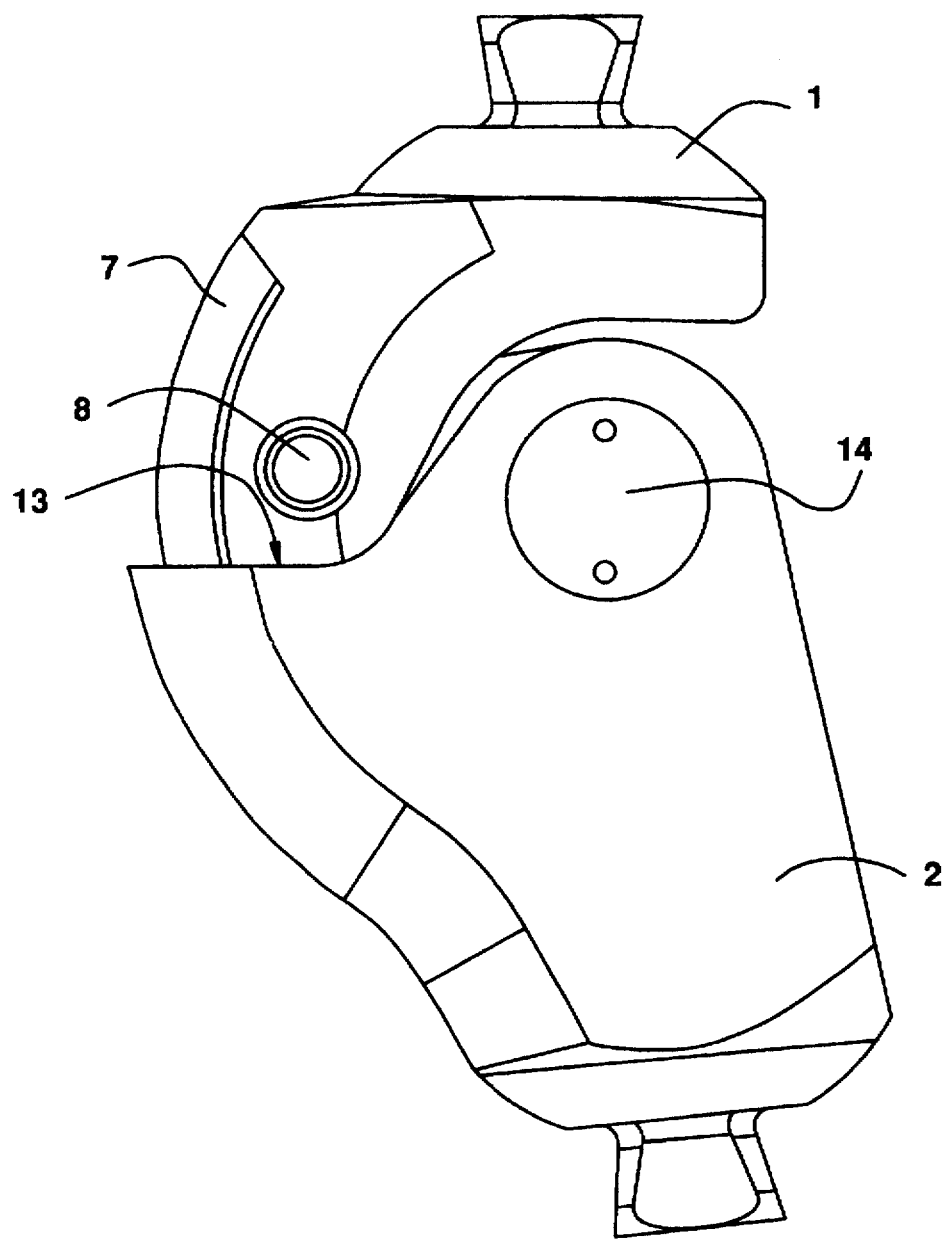
FIG. 1 is a side elevation view of a knee brake joint in an extended position in accordance with the invention.
Figure 2:
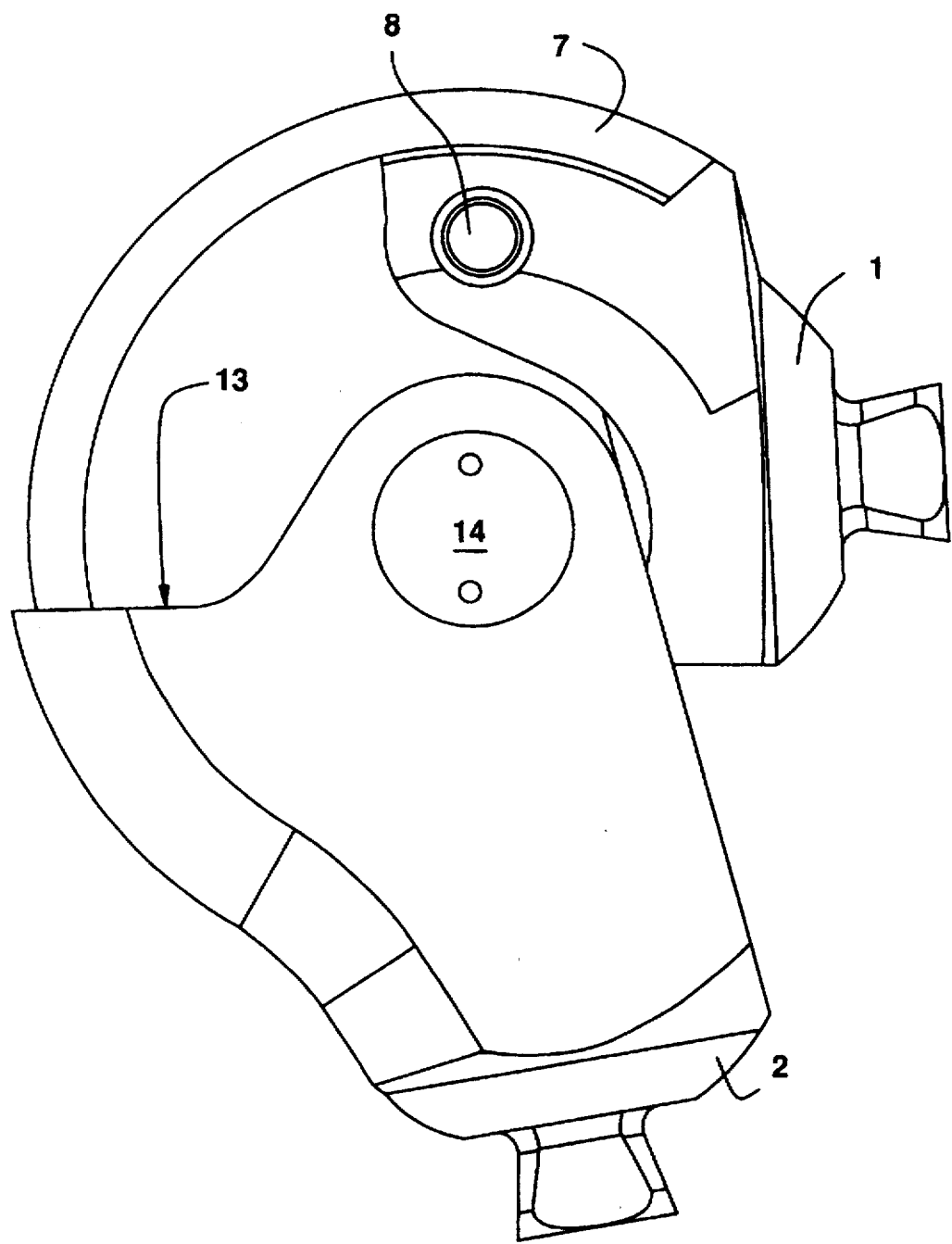
FIG. 2 is a side elevation view of the knee brake joint in a flexed position.
Figure 3:
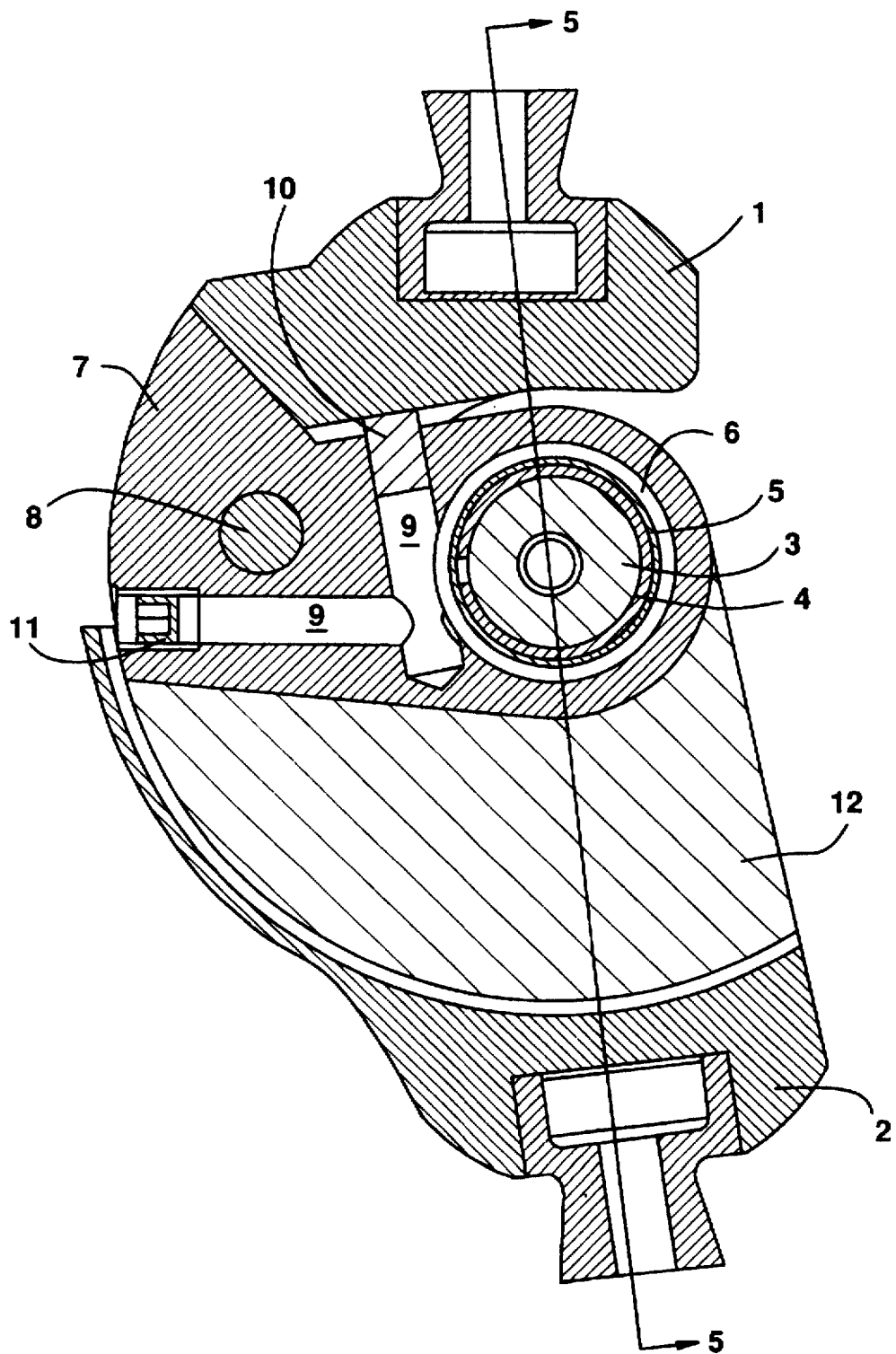
FIG. 3 is a side elevation view, in longitudinal cross section of the knee brake joint.
Figure 4:
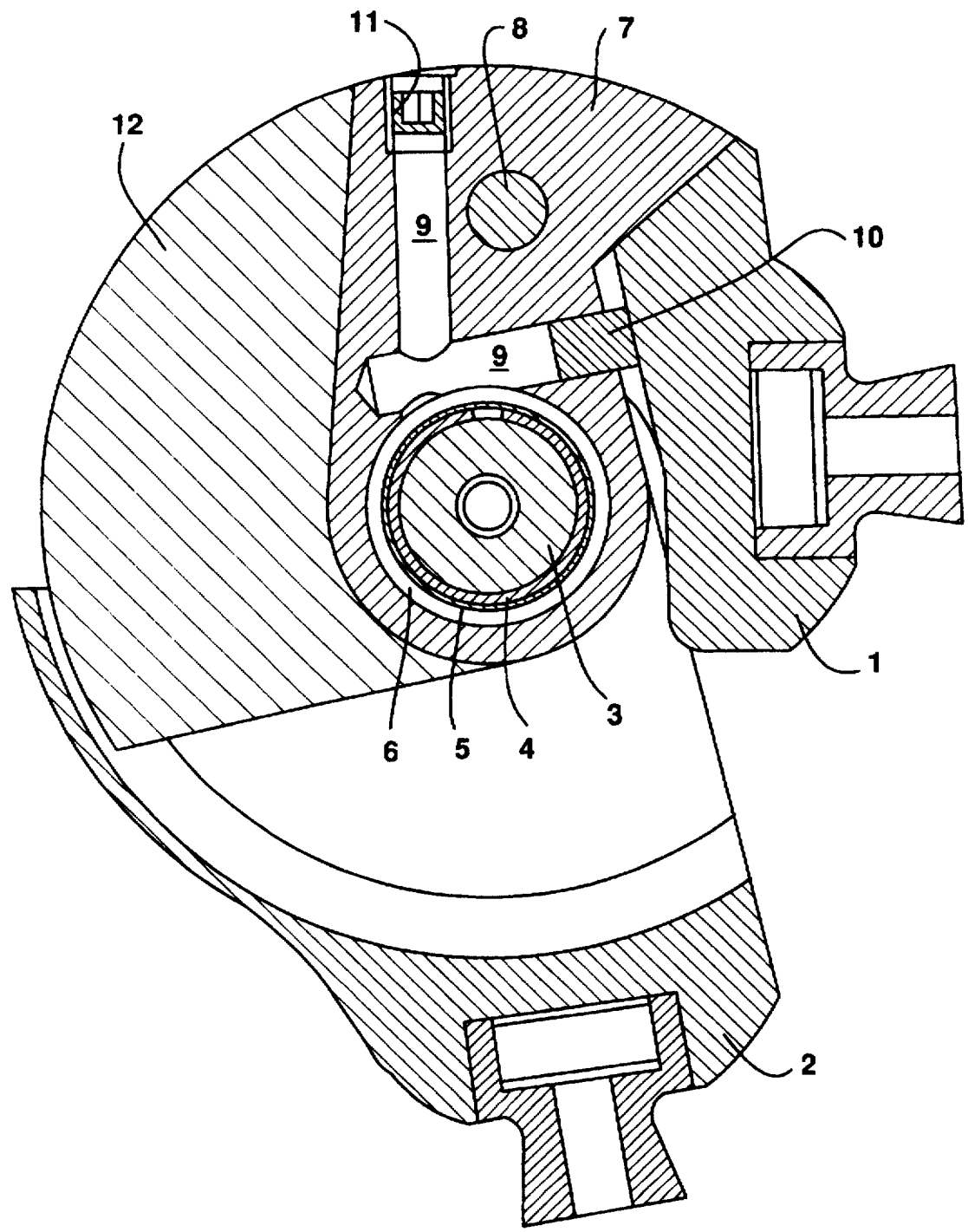
FIG. 4 is a side elevation view, in longitudinal cross section of the knee brake joint.
Figure 5:
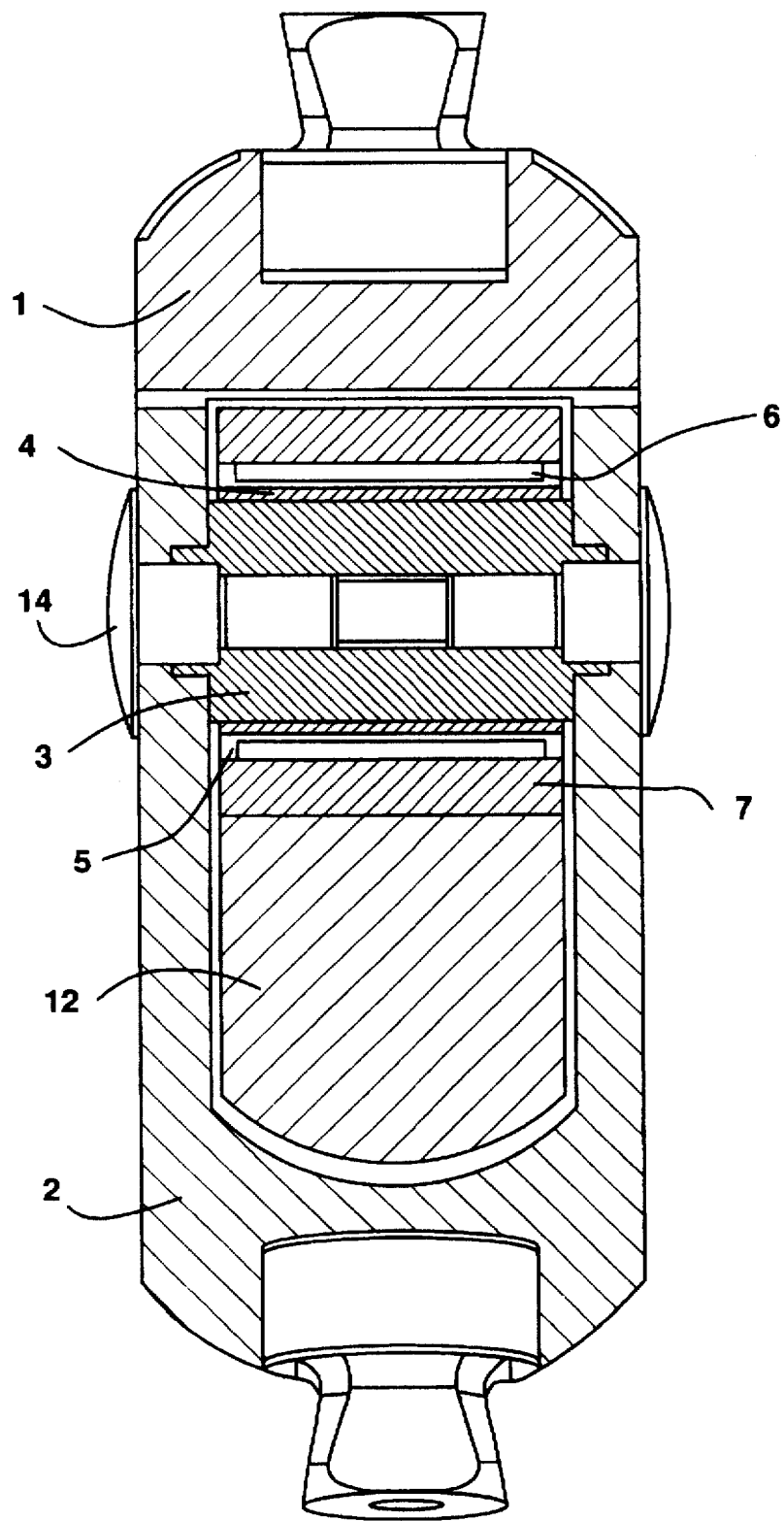
FIG. 5 is a cross-sectional view taken along line 5—5 in FIG. 3.

Referring now to FIGS. 1–5, wherein like numerals indicate like parts, there will be seen a knee brake joint in accordance with a preferred embodiment of the invention. The knee brake joint includes an upper joint portion 1, a lower joint portion 2, and a joint shaft 3 which connects these two joint portions pivotably to one another. The lower joint portion 2 is connected to the joint shaft 3 for fixed rotation with the joint shaft 3. The joint shaft 3 is designed as, and operates as, a brake shaft. A brake bushing 4, which may have a slotted design, rotates about the joint shaft 3 and serves as a bearing. The brake bushing 4 is anchored in an compression sleeve 5 for fixed rotation with the compression sleeve 5. An annular brake chamber 6 surrounds the joint shaft 3. The compression sleeve 5 seals the joint shaft 3 off from the annular brake chamber 6 in a liquid-tight manner.

The brake bushing 4 and the compression sleeve 5 are connected to a clamping or support portion 7 for fixed rotation with the clamping or support portion 7. The upper joint portion 1 is mounted on the clamping or support portion 7 in an articulated manner via a pivot axle 8. The upper joint portion 1 is pivotable to a limited extent about the pivot axle 8.

The brake chamber 6 communicates, for purposes of fluid exchange, with a hollow space 9 which is closed off on all sides by the clamping or support portion 7, a pressure piston 10, and an adjusting screw 11. The hollow space 9 is integrated into the clamping or support portion 7 and is filled with an incompressible medium, such as oil. The pressure piston 10, which is mounted in a longitudinal guide in the clamping or support portion 7 and seals the incompressible medium in the clamping or support portion 7, protrudes into this hollow space 9. An inner end of pressure piston 10 impacts, or contacts, the incompressible medium. An opposite end of the pressure piston 10 protrudes from the clamping or support portion 7 and serves as a limit stop for the upper joint portion 1.

An adjusting screw 11 arranged in, and mounted in, the clamping or support portion 7 also protrudes into the hollow space 9. By manually adjusting this screw 11, it is possible to preset and reset the pressure of the incompressible medium in the hollow space 9.

A knee cap portion 12, which serves to give shape to the knee when the knee is flexed (see FIGS. 2 and 4), is securely connected to the clamping or support portion 7. An extension limit stop 13 defines the extension position, (see FIGS. 1 and 3) and thus the movement of, the prosthetic knee joint. A shaft screw 14, shown in FIG. 1, connects the joint shaft 3 to the lower joint portion 2.

Under loading, the upper joint portion 1 pivots about the pivot axle 8, and presses on the pressure piston 10. As a consequence of this load-dependent actuation, the pressure piston 10 applies pressure to the incompressible medium located in the hollow space 9. This application of pressure occurs after the initial pressure has previously been adjusted and set by positioning the adjusting screw 11. Under the increased pressure applied to the incompressible medium, fluid pressure impacts and compresses the compression sleeve 5 in the brake chamber 6 over its entire periphery. This in turn compresses the brake bushing 4 concentrically enclosed by the expansion sleeve 5. The brake bushing 4 then compresses against the joint shaft 3 to brake rotational movement of the prosthetic knee joint. In this way, braking is achieved in relation to the joint shaft 3 and, thus, in relation to relative pivoting between the upper joint portion 1 and the lower joint portion 2.

After reading and understanding the foregoing inventive prosthetic brake joint, in conjunction with the drawings, it will be appreciated that several distinct advantages of the subject invention are obtained.

In accordance with the invention, the incompressible medium transmits a uniform force over the entire circumference of the brake bushing. This translates into a uniform application of braking force to the brake bushing and the joint shaft. The uniform application of braking force results in high braking performance, even at relatively low braking pressure. In addition, the uniform application of braking force reduces wear and tear on the prosthetic brake joint components, particularly the brake bushing. A further advantage is that pretensioning of the prosthetic knee joint and presetting or resetting of pressure applied by the incompressible medium to the brake bushing can be effected by tightening or loosening the adjusting screw. Additionally, the closed design of the braking parts results in a stable joint structure with a higher rigidity of connection. Moreover, because the brake bushing is surrounded by an compression sleeve, it possible to use an axially slotted brake bushing in the subject invention.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A prosthetic brake joint comprising:

an upper joint portion;

a lower joint portion;

a support portion to which said upper joint portion is mounted;

a pivot axle about which said upper joint portion is pivotal to a limited extent relative to said support portion;

a joint shaft, said lower joint portion being connected to said joint shaft for fixed rotation with said joint shaft, said joint shaft pivotally connecting said upper joint portion and said support portion to said lower joint portion;

a brake bushing surrounding said joint shaft, said brake bushing being rotatable about said joint shaft and serving as a bearing, said support portion being connected to said brake bushing for fixed rotation with said brake bushing an annular brake chamber surrounding said brake bushing, said annular brake chamber being adapted to be filled with an incompressible medium and communicating, for purposes of fluid exchange, with a closed hollow space integrated in said support portion;

a pressure piston mounted to said support portion and supporting said upper joint portion, said pressure piston protruding into said closed hollow space and adapted to operably impact the incompressible medium; and a compression sleeve surrounding said brake bushing and adapted so that, when said pressure piston is depressed, pressure is applied to the incompressible medium which is adapted to compress said compression sleeve against said brake bushing and thereby compress said brake bushing against said joint shaft to exert a braking force on said joint shaft.

2. The prosthetic brake joint as claimed in claim 1 wherein said prosthetic brake joint forms a knee brake joint for a leg prothesis.

3. The prosthetic brake joint as claimed in claim 1 wherein said joint shaft performs as a brake shaft.

4. The prosthetic brake joint as claimed in claim 1 wherein said compression sleeve is connected to said brake bushing for fixed rotation with said support portion.

5. The prosthetic brake joint as claimed in claim 4 wherein said brake bushing is anchored in said compression sleeve for fixed rotation with said compression sleeve.

6. The prosthetic brake joint as claimed in claim 4 and further comprising:

an adjusting screw arranged in said support portion and protruding into said closed hollow space.

7. The prosthetic brake joint as claimed in claim 1 wherein said brake bushing is anchored in said compression sleeve for fixed rotation with said compression sleeve.

8. The prosthetic brake joint as claimed in claim 7 and further comprising:

an adjusting screw arranged in said support portion and protruding into said closed hollow space.

9. The prosthetic brake joint as claimed in claim 1 and further comprising:

an adjusting screw arranged in said support portion and protruding into said closed hollow space.

* * * * *